(12) United States Patent
Matthews et al.

(10) Patent No.: US 6,190,650 B1
(45) Date of Patent: Feb. 20, 2001

(54) ANTIVIRAL DENDRIMERS

(75) Inventors: Barry Ross Matthews, Olinda; George Holan, Brighton, both of (AU)

(73) Assignee: Biomolecular Research Institute Ltd., Parkville (AU)

(*) Notice: Under 35 U.S.C. 154(b), the term of this patent shall be extended for 0 days.

(21) Appl. No.: 08/765,528

(22) PCT Filed: Jun. 15, 1995

(86) PCT No.: PCT/AU95/00350

§ 371 Date: Apr. 28, 1997

§ 102(e) Date: Apr. 28, 1997

(87) PCT Pub. No.: WO95/34595

PCT Pub. Date: Dec. 21, 1995

(30) Foreign Application Priority Data

Jun. 15, 1994 (AU) .................................................. PM 6239

(51) Int. Cl.⁷ ........................ A61K 31/78; A61K 31/785; C08G 73/00
(52) U.S. Cl. ..................................... 424/78.17; 424/78.27; 424/78.29; 424/DIG. 16; 525/512; 525/513; 525/514
(58) Field of Search ............................... 424/78.08, 78.18, 424/78.27, 78.29, DIG. 16; 525/512–514

(56) References Cited

U.S. PATENT DOCUMENTS 5,229,490   7/1993   Tam .

FOREIGN PATENT DOCUMENTS

| 2435484 | 8/1984 | (AU) . |
| 4906585 | 6/1986 | (AU) . |
| 7715987 | 3/1988 | (AU) . |
| 1240095 | 1/1995 | (AU) . |
| 0328403 | 8/1989 | (EP) . |
| 0339695 | 11/1989 | (EP) . |
| 9303766 | 3/1993 | (WO) . |

OTHER PUBLICATIONS

Roy Rene et al., "Solid–Phase Synthesis of Dendritic Sialoside Inhibitor of Influenza A Virus Hemagglutinin," Journal of the Chemical Society, Chemical Communications, 24: 1869–1872 (1993).

*Primary Examiner*—Edward J. Webman
(74) *Attorney, Agent, or Firm*—Foley & Lardner

(57) ABSTRACT

An antiviral compound comprises a dendrimer such as a polyamidoamine or polylysine dendrimer having a plurality of terminal groups, wherein at least one of the terminal groups has an anionic- or cationic-containing moiety bonded thereto, particularly a sulfonic acid-containing, carboxylic acid-containing or trimethylammonium-containing moiety or the like.

40 Claims, 1 Drawing Sheet

ANTIVIRAL DENDRIMERS

FIELD OF THE INVENTION

This invention relates to antiviral agents, and in particular it relates to dendrimers which have been found to have significant antiviral activity against human immunodeficiency virus (HIV) and other enveloped viruses.

BACKGROUND OF THE INVENTION

It has been established that certain sulfonated polysaccharide compounds have antiviral activity when screened against HIV, however these compounds are relatively unstable and accordingly large amounts of these compounds are required to obtain effective antiviral effects. In addition, many of these compounds, including heparin and dextran sulfate for example, are potent anticoagulants and because of this activity they are not particularly suited for clinical use as antiviral agents.

The present invention provides a new class of antiviral agents based on a particular type of polymer referred to herein as a "dendrimer", which have substantial antiviral activity against HIV1 and HIV2, CMV and HSV, and which have substantially no anticoagulant activity. These compounds are therefore well suited for prophylactic and therapeutic use as antiviral agents in humans.

SUMMARY OF THE INVENTION

According to the present invention, there is provided an antiviral compound comprising a dendrimer having a plurality of terminal groups wherein at least one of said terminal groups has an anionic- or cationic-containing moiety, other than a 2-thiosialic acid moiety, bonded thereto.

Such a dendrimer is referred to here in as an "anionic or cationic dendrimer", and this term is used throughout this specification and the claims which follow to include not only the dendrimers per se, but also their pharmaceutically or veterinarily acceptable salts, for example the alkaline metal or alkaline earth metal salts such as the sodium, potassium or calcium salts.

DETAILED DESCRIPTION OF THE INVENTION

Figure 1:
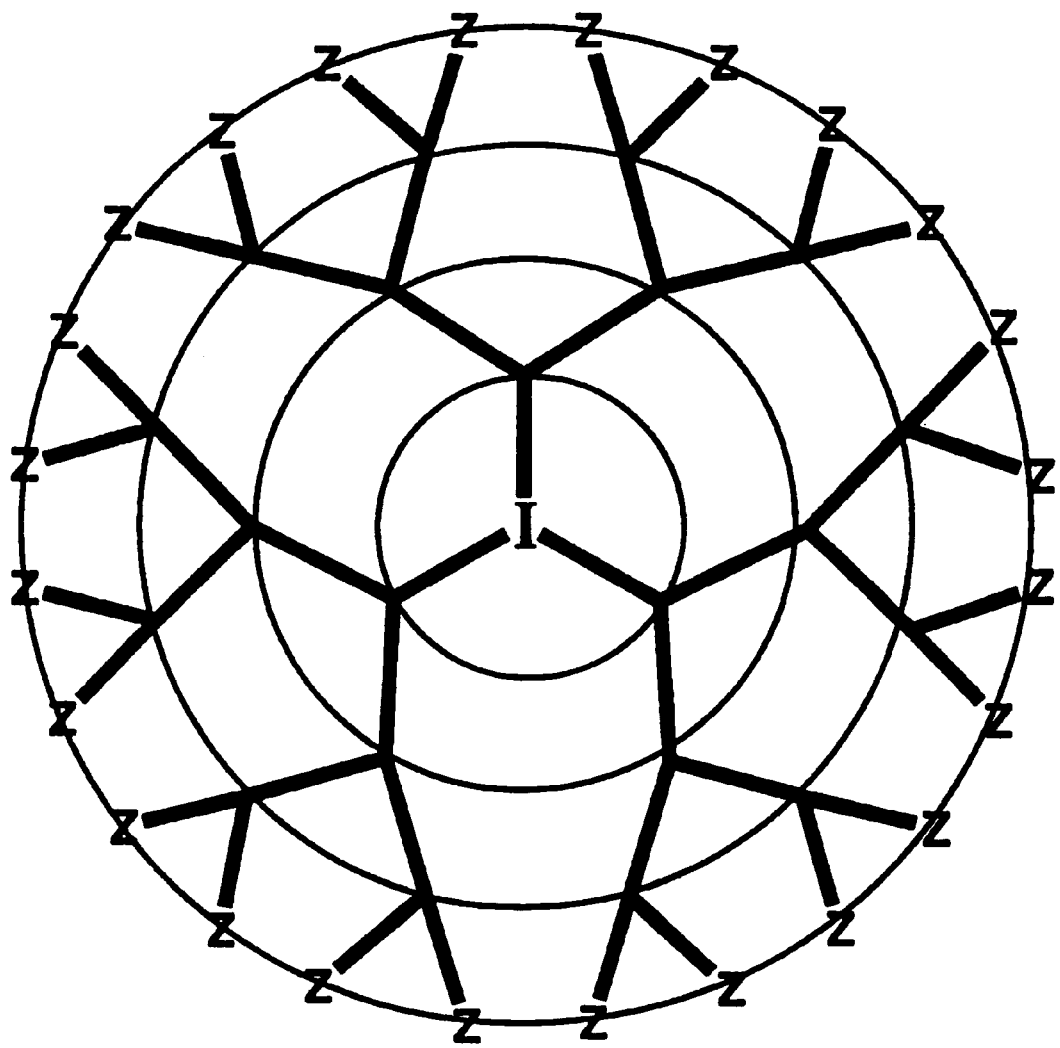
FIG. 1 shows a dendrimer with bound ionic moieties Z.

Dendrimers are macromolecular highly branched compounds formed by reiterative reaction sequences starting from an initial, core molecule with successive layers or stages being added in successive "generations" to build up a three-dimensional, highly ordered polymeric compound. A generalised dendrimer structure is shown in FIG. 1. Dendrimers are characterised by the following features: i an initiator core(I) which may have one or more reactive sites and be point-like or of significant size so as to effect the final topology of the dendrimer; ii layers of branched repeating units attached to the initiator core; iii functional terminal groups(Z) attached to the surface of the dendrimer. The present invention uses dendritic structures as frameworks for the attachment of ionic moieties; the invention is not limited to the spherical dendrimers described in detail herein but can be based on any dendritic structure. The variety of dendrimers in both shape and constitution are well known to persons skilled in the art.

The preparation of dendrimers is well known, and is described by way of example in U.S. Pat. Nos. 4,289,872 and 4,410,688 (describing dendrimers based on layers of lysine units), as well as U.S. Pat. Nos. 4,507,466, 4,558,120, 4,568,737 and 4,587,329 (describing dendrimers based on other units including polyamidoamine or PAMAM dendrimers). The dendrimers disclosed in these US patents are described as being suitable for uses such as surface modifying agents, as metal chelating agents, as demulsifiers or oil/water emulsions, wet strength agents in the manufacture of paper, and as agents for modifying viscosity in aqueous formulations such as paints. It is also suggested in U.S. Pat. Nos. 4,289,872 and 4,410,688 that the dendrimers based on lysine units can be used as substrates for the preparation of pharmaceutical dosages.

International Patent Publications Nos. WO 88/01178, WO 88/01179 and WO 88/01180 disclose conjugates in which a dendrimer is conjugated or associated with another material such as a carried pharmaceutical or agricultural material. These patent publications together with the U.S. patents mentioned above contain a broad disclosure of various dendrimers and processes for the preparation thereof, and the disclosure of each of these publications is incorporated herein by reference.

The term "dendrimer" as used herein is to be understood in its broadest sense, and to include within its scope all forms and compositions of these dendrimers as disclosed in Patent Publications Nos. WO 88/01178, WO 88/01179 and WO 88/01180. The term also includes linked or bridged dendrimers as disclosed in these patent publications.

The preferred dendrimers of the present invention comprise a polyvalent core covalently bonded to at least two dendritic branches, and preferably extend through at least two generations. Particularly preferred dendrimers are polyamidoamine (PAMAM) dendrimers, PAMAM (EDA) dendrimers and polylysine dendrimers.

In accordance with the present invention, at least one, and preferably a substantial number, of the terminal groups on the surface of the dendrimer has an anionic- or cationic-containing moiety covalently bonded thereto. The branches of the dendrimer may terminate in amino groups or other functional reactive groups such as OK, SH, or the like, which subsequently can be reacted with the cationic and anionic moieties forming the outer layer of the dendrimer. Where the terminal groups of the dendrimer are amine groups, the anionic- or cationic-containing moiety may be bonded to the dendrimer by a variety of functional groups including amide and thiourea linkages. Preferred anionic- or cationic-containing moieties which may be bonded to the terminal groups of the dendrimer include sulfonic acid-containing moieties, carboxylic acid-containing moieties other than 2-thiosialic acid moieties, trimethylammonium-containing moieties and polyamino-macrocycle-containing moieties.

Suitable anionic- and cationic-containing moieties which may be bonded to the amino or other terminal groups of dendrimers include, by way of example, the following groups (in which n is zero or a positive integer, more particularly n is zero or an integer of from 1 to 20):

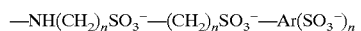

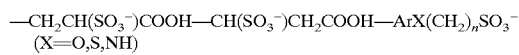

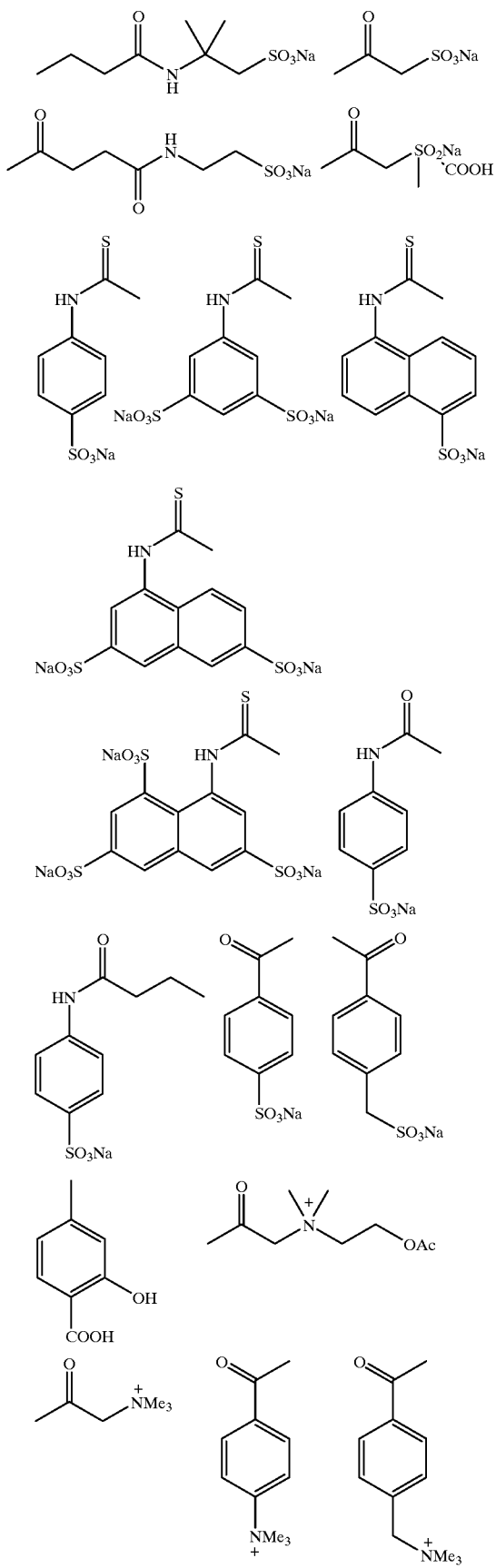
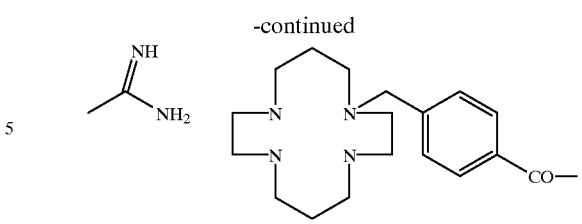

Particular moieties which may be bonded to the terminal groups of the dendrimer in accordance with this invention include alkyl sulfonic acid groups; supfoacetamide groups; sulfosuccinamic acid groups; N-sulfoalkyl succinamide groups, such as N-(2-sulfoethyl)succinamide groups; aryl or heteroaryl thioureas substituted with one or more sulfonic acid groups, such as 4-sulfophenylthiourea groups, 3,6-disulfonapthylthiourea groups, 4-sulfonapthylthiourea groups, 3,5-disulfophenyl thiourea groups and 3,6,8-trisulfonapthylthiourea groups; aryl or heteroaryl amides substituted with one or more sulfonic acid, sulfoalkyl, sulfoalkoxy, sulfoalkylamino or sulfoalkylthio groups, such as 4-(sulfomethyl) benzamide groups or 4-sulfobenzamide groups; aryl or heteroaryl alkanamides substituted with one or more sulfonic acid groups, such as N-(4-sulfophenyl) propanamide groups; aryl or heteroaryl ureas substituted with one or more sulfonic acid groups, such as 4-sulfophenyl urea groups; N,N,N-trimethyl derivatives of amino acids, such as N,N,N-trimethylglycinamine groups; aryl or heteroarylamides substituted with one or more trialkylamino, trialkylaminoalkyl, trialkylaminoalkyloxy, trialkylaminoalkylamino or trialkylaminoalkylthio groups, such as 4-trimethylammonium benzamide or 4-(trimethylammonium methyl) benzamide groups; N-(2-acetoxyethyl)-N,N-(dimethylammonium) methylcarboxamide groups; guanidino groups; 4-carboxy-3-hydroxybenzylamine groups; or macrocyclic polyamino groups containing one or more macrocyclic rings connected through an alkyl or aryl spacer moiety to the terminal group of the dendrimer, such as 4-([1,4,8,11-terayclotetradecane] methyl)benzamide groups.

The anionic or cationic dendrimers of this invention may be prepared by standard chemical methods which are well known to persons skilled in this art. Suitable methods are described by way of example in Examples 1 to 20 below.

As previously described, the anionic or cationic dendrimers of the present invention have been found to exhibit significant antiviral activity, particularly against HIV. Accordingly, these anionic or cationic dendrimers are useful in prophylactic and therapeutic treatment of viral infections, for example infections by HIV1 and HIV2 and other enveloped viruses including flaviviruses such as Hepatitis B and Hepatitis C, Bovine Viral Diarrhoea Virus, Human Influenza Virus A and B, Rhinovirus, Human Parainfluenza Virus, Respiratory Syncytial Virus (RSV), Varicella Zoster Virus (VZV), Human Cytomegalovirus (CMV), Epstein Barr Virus (EBV), Human Papilloma Virus (HPV), Adenovirus-8, Herpes Simplex Virus (HSV) type 1 and 2, Measles Virus, and Vesicular Stomatitis Virus (VSV).

Thus, in another aspect the present invention provides a pharmaceutical or veterinary composition for prophylactic or therapeutic antiviral treatment of a human or non-human animal, which comprises an anionic or cationic dendrimer as broadly described above, in association with at least one pharmaceutically or veterinarily acceptable carrier or diluent.

The formulation of such compositions is well known to persons skilled in this field. Suitable pharmaceutically acceptable carriers and/or diluents include any and all conventional solvents, dispersion media, fillers, solid carriers, aqueous solutions, coatings, antibacterial and antifungal agents, isotonic and absorption delaying agents, and the like. The use of such media and agents for pharmaceutically active substances is well known in the art, and it is described, by way of example, in Remington's Pharmaceutical Sciences, 18th Edition, Mack Publishing Company, Pennsylvania, USA. Except insofar as any conventional media or agent is incompatible with the active ingredient, use thereof in the pharmaceutical compositions of the present invention is contemplated. Supplementary active ingredients can also be incorporated into the compositions.

It is especially advantageous to formulate compositions in dosage unit form for ease of administration and uniformity of dosage. Dosage unit form as used herein refers to physically discrete units suited as unitary dosages for the human subjects to be treated; each unit containing a predetermined quantity of active ingredient calculated to produce the desired therapeutic effect in association with the required pharmaceutical carrier and/or diluent. The specifications for the novel dosage unit forms of the invention are dictated by and directly dependent on (a) the unique characteristics of the active ingredient and the particular therapeutic effect to be achieved, and (b) the limitations inherent in the art of compounding such an active ingredient for the particular treatment.

In another aspect, the present invention provides a method for prophylactic or therapeutic treatment of an HIV or other viral infection in a human or non-human animal, which comprises administering to said human or animal a prophylactic- or therapeutic-antiviral-effective amount of an anionic or cationic dendrimer as broadly described above.

In yet another aspect, this invention provides the use of a prophylactic- or therapeutic-antiviral-effective amount of an anionic or cationic dendrimer as broadly described above in the prophylactic or therapeutic treatment of, or in the manufacture of a medicament for prophylactic or therapeutic treatment of an HIV or other viral infection in a human or non-human animal.

A variety of administration routes are available. The particular mode selected will depend, of course, upon the particular condition being treated and the dosage required for therapeutic efficacy. The methods of this invention, generally speaking, may be practised using any mode of administration that is medically acceptable, meaning any mode that produces therapeutic levels of the active component of the invention without causing clinically unacceptable adverse effects. Such modes of administration include oral, rectal, topical, nasal, transdermal or parenteral (e.g. subcutaneous, intramuscular and intravenous) routes. Formulations for oral administration include discrete units such as capsules, tablets, lozenges and the like. Other routes include intrathecal administration directly into spinal fluid, direct introduction such as by various catheter and balloon angioplasty devices well known to those of ordinary skill in the art, and intraparenchymal injection into targeted areas.

The compositions may conveniently be presented in unit dosage form and may be prepared by any of the methods well known in the art of pharmacy. Such methods include the step of bringing the active component into association with a carrier which constitutes one or more accessory ingredients. In general, the compositions are prepared by uniformly and intimately bringing the active component into association with a liquid carrier, a finely divided solid carrier, or both, and then, if necessary, shaping the product.

Compositions of the present invention suitable for oral administration may be presented as discrete units such as capsules, cachets, tablets or lozenges, each containing a predetermined amount of the active component, in liposomes or as a suspension in an aqueous liquor or non-aqueous liquid such as a syrup, an elixir, or an emulsion.

Compositions suitable for parenteral administration conveniently comprise a sterile aqueous preparation of the active component which is preferably isotonic with the blood of the recipient. This aqueous preparation may be formulated according to known methods using those suitable dispersing or wetting agents and suspending agents. The sterile injectable preparation may also be a sterile injectable solution or suspension in a non-toxic parenterally-acceptable diluent or solvent, for example as a solution in polyethylene glycol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono-or di-glycerides. In addition, fatty acids such as oleic acid find use in the preparation of injectables.

Other delivery systems can include sustained release delivery systems. Preferred sustained release delivery systems are those which can provide for release of the active component of the invention in sustained release pellets or capsules. Many types of sustained release delivery systems are available. These include, but are not limited to: (a) erosional systems in which the active component is contained within a matrix, and (b) diffusional systems in which the active component permeates at a controlled rate through a polymer. In addition, a pump-based hardware delivery system can be used, some of which are adapted for implantation.

The active component is administered in prophylactically or therapeutically effective amounts. A prophylactically or therapeutically effective amount means that amount necessary at least partly to attain the desired effect, or to delay the onset of, inhibit the progression of, or halt altogether, the onset or progression of the particular condition being treated. Such amounts will depend, of course, on the particular condition being treated, the severity of the condition and individual patient parameters including age, physical condition, size, weight and concurrent treatment. These factors are well known to those of ordinary skill in the art and can be addressed with no more than routine experimentation. It is preferred generally that a maximum dose be used, that is, the highest safe dose according to sound medical judgement. It will be understood by those of ordinary skill in the art, however, that a lower dose or tolerable dose may be administered for medical reasons, psychological reasons or for virtually any other reasons.

Generally, daily oral doses of active component will be from about 0.01 mg/kg per day to 1000 mg/kg per day. Small doses (0.01–1 mg) may be administered initially, followed by increasing doses up to about 1000 mg/kg per day. In the event that the response in a subject is insufficient at such doses, even higher doses (or effective higher doses by a different, more localised delivery route) may be employed to the extent patient tolerance permits. Multiple doses per day are contemplated to achieve appropriate systemic levels of compounds.

Throughout this specification and the claims which follow, unless the context requires otherwise, the word "comprise", or variations such as "comprises" or "comprising", will be understood to imply the inclusion of a stated integer or group of integers but not the exclusion of any other integer or group of integers.

Further features of the present invention will be apparent from the following Examples which are included by way of illustration, not limitation of the invention. In the following Examples, PAMAM dendrimers refer to polyamidoamine dendrimers based on an ammonia core as detailed in U.S. Pat. Nos. 4,507,466, 4,558,120, 4,568,737 and 4,587,329; PAMAM (EDA) dendrimers refer to polyamidoamine dendrimers based on an ethylene diamine core; and BHAlys$_x$-lys$_y$lys$_z$ dendrimers refer to polylysine unsymmetrical dendrimers based on a benzhydrylamine core and lysine branching units as described in U.S. Pat. Nos. 4,289,872 and 4,410,688. The polyamidoamine dendrimers PAMAM 1.0, PAMAM 2.0, PAMAM 3.0, PAMAM 4.0, PAMAM 5.0 or higher generation, PAMAM 4.0 (EDA), and the polylysine dendrimers BHAlyslys$_2$, BHAlyslys$_2$lys$_4$, BHAlyslys$_2$lys$_4$lys$_8$ and BHAlyslys$_2$lys$_4$lys$_8$lys$_{16}$, BHAlyslys$_2$lys$_4$lys$_8$lys$_{16}$lys$_{32}$, BHAlyslys$_2$lys$_4$lys$_8$lys$_{16}$lys$_{32}$lys$_{64}$, or higher generations are prepared as described in U.S. Pat. Nos. 4,289,872, 4,410,688, 4,507,466, 4,558,120, 4,568,737 and 4,587,329 and International Patent Publications Nos. WO 88/01178, WO 88/01179 and WO 88/01180 referred to above.

EXAMPLE 1

Reaction of polymers with 2-acrylamido-2-methyl propane sulfonic acid to give sulfonic acid terminated dendrimers.

A. PAMAM 1.0

Solid sodium carbonate (0.13 g; 1.0 mmol) was added slowly to a stirred solution of 2-acrylamido-2-methyl propane sulfonic acid (0.41 g; 2.0 mmol) in water (3 ml). After the evolution of gas had ceased, the pH of the solution was 8.0. A solution of PAMAM 1.0 (0.12 g; 0.33 mmol) in water (1 ml) was then added to the solution followed by the addition of four drops of a 40% aq. solution of benzyl trimethylammonium hydroxide. The solution was then heated under nitrogen at 60° for three days and then concentrated. The residue was purified by gel filtration (Sephadex G10; water) and then freeze dried to give the sulfonated PAMAM 1.0 dendrimer as an off-white solid (0.51 g). $^1$H and $^{13}$C nmr spectra showed a mixture of dialkylated and monoalkylated PAMAM 1.0 dendrimer (ca. 70:30). $^{13}$C nmr (D$_2$O): δ 31.0, 31.1, 37.1, 37.7, 41.3, 48.6, 51.5, 53.1, 53.4, 55.6, 56.2, 61.2, 61.5, 178.3, 179.0, 179.8.

B. PAMAM 2.0 (Compound No. 20)

PAMAM 2.0 was reacted with 2-acrylamido-2-methyl propane sulfonic acid as described above. The crude product was purified by gel filtration (Sephadex G10; water) and then freeze dried to give an off-white solid. $^1$H and $^{13}$C nmr spectra showed a mixture of dialkylated and monoalkylated PAMAM 2.0 dendrimer (ca 65:35). $^{13}$C nmr (D$_2$O): δ 31.0, 31.1, 37.1, 37.7, 41.3, 48.7, 51.5, 53.4, 55.6, 56.2, 61.2, 61.5, 178.4, 179.0, 179.1, 179.6. When the above reaction was repeated omitting the benzyltrimethyl-ammonium hydroxide a similar result was obtained.

C. PAMAM 3.0

PAMAM 3.0 was reacted with 2-acrylamido-2-methyl propane sulfonic acid as above except that a slight excess of sodium carbonate was used and the benzyltrimethylammonium hydroxide was omitted. $^1$H and $^{13}$C nmr spectra showed a mixture of dialkylated and monoalkylated PAMAM 3.0 dendrimer (ca. 50:50). $^{13}$C nmr (D$_2$O): δ 31.0, 31.1, 36.9, 37.4, 41.1, 48.6, 51.5, 53.4, 55.7, 56.2, 61.1, 61.5, 178.2, 178.9, 179.0, 179.8.

D. PAMAM 4.0

PAMAM 4.0 was reacted with 2-acrylamido-2-methyl propane sulfonic acid as described for PAMAM 3.0. $^1$H and $^{13}$C nmr spectra showed a mixture of dialkylated and monoalkylated PAMAM 4.0 dendrimer (ca. 35:65). $^{13}$C nmr (D$_2$O): δ 31.0, 31.1, 36.9, 37.3, 41.1, 48.5, 51.5, 53.5, 55.7, 56.2, 61.1, 61.5, 178.1, 178.9, 179.0, 179.8.

EXAMPLE 2

Preparation of sodium sulfoacetamide terminated dendrimers.

A. PAMAM 1.0

A solution of 4-nitrophenyl bromoacetate (0.40 g; 1.5 mmol) in dry DMF (1 ml) was added to a stirred solution of PAMAM 1.0 (0.18 g; 0.5 mmol) in DMF (3 ml). The resulting yellow solution was stirred for 20 hours at room temperature, when a ninhydrin test was negative. The solution was concentrated (30°/0.1 mmHg) to give a yellow oil. This oil was partitioned between water and chloroform and the aqueous layer separated and washed with chloroform (2×) and finally with ethyl acetate. The aqueous solution was concentrated (35°/25 mmHg) to give the bromoacetylated PAMAM 1.0 dendrimer as a yellow oil (0.36 g; 100%). $^{13}$C nmr (D$_2$O): δ 32.8, 33.3, 43.0, 43.5, 54.4, 174.5, 176.4.

A solution of sodium sulfite (0.2 g; 1.6mmol) in water (1 ml) was added to a solution of the bromoacetylated PAMAM 1.0 dendrimer described above (0.36 g; 0.5 mmol) in water (5 ml) and the solution left to stand at room temperature for eleven days. The yellow solution was concentrated to give a yellowish solid (0.60 g). $^{13}$C nmr (D$_2$O): δ 34.4, 43.1, 43.4, 54.0, 61.7, 171.3, 177.2.

The above reaction sequence could be carried out without isolating the bromoacetylated dendrimer by simply adding the sodium sulfite solution to the crude aqueous extract obtained from the first reaction.

B. PAMAM 2.0

Method 1:

A solution of 4-nitrophenyl bromoacetate (0.18 g; 0.7 mmol) in dry DMF (1 ml) was added to a stirred solution of PAMAM 2.0 (0.10 g; 0.1 mmol) in DMF (3 ml). The resulting yellow solution was stirred for 20 hours at room temperature, when a ninhydrin test was negative. The solution was then added with swirling to water (150 ml) and the mixture extracted with chloroform (3×) and ethyl acetate. A solution of sodium sulfite (0.1 g; 0.8 mmol) in water (1 ml) was added to the crude bromoacetylated dendrimer solution and the mixture allowed to stand for three days at room temperature. The yellowish solution was then concentrated to give a yellow solid residue, which was purified by gel filtration (Sephadex LH20; water) to give the sodium sulfoacetamide terminated PAMAM 2.0 dendrimer (103 mg). $^{13}$C nmr (D$_2$O): δ 33.0, 35.7, 36.0, 37.7, 40.3, 43.0, 43.2, 53.4, 53.7, 56.0, 61.6, 171.2, 174.6, 178.5.

Method 2:

Solid succinimidyl acetylthioacetate (67 mg; 0.33 mmol) was added to a solution of PAMAM 2.0 (52 mg; 0.05 mmol) in dry DMF (2 ml) and the resulting solution stirred at room temperature for two days. The mixture was then concentrated (30°/10$^{-3}$ mmHg) to give an oily residue. The residue was partitioned between water and chloroform, and the water layer separated and concentrated to give a viscous oil (117 mg). $^1$H and $^{13}$C nmr showed the oil to be a mixture of the acylated dendrimer and N-hydroxy succinimide. Gel filtration (Sephadex G10; water) provided a pure sample of the acetylthioacetamide terminated PAMAM 2.0 dendrimer (29 mg). $^{13}$C nmr (D$_2$O): δ 34.0, 34.2, 37.3, 43.0, 43.1, 43.3, 53.5, 54.0, 56.3, 175.4, 177.2, 177.5.

A solution of the above functionalised dendrimer in 40% aqueous formic acid (7 ml) was then added to an ice cold freshly prepared solution of performic acid (1.6 mmol) in formic acid (2 ml). The mixture was stirred for one hour at 0° and then for twenty hours at room temperature. A small amount of activated charcoal was then added to decompose any excess peracid, the mixture stirred for 30 minutes then filtered and concentrated to give a viscous oil. The crude product was dissolved in water, the pH adjusted to 9.0 with aqueous sodium bicarbonate and the material desalted by passage through a column of Sephadex G10. A white solid (20 mg;) was obtained after lyophylisation which was spectroscopically essentially the same as the material obtained by method 1. $^{13}$C nmr (D$_2$O): δ 33.0, 38.7, 42.9, 43.0, 43.1, 53.9, 54.3, 56.5, 61.6, 171.2, 176.4, 177.0.

EXAMPLE 3

Preparation of sodium sulfosuccinamic acid terminated dendrimers

A. PAMAM 1.0

Solid maleic anhydride (0.11 g; 1.1 mmol) was added to a stirred solution of PAMAM 1.0 (0.12 g; 0.33 mmol) in dry DMF (3 ml). The mixture became a little warm and brownish as the anhydride dissolved and the resulting solution was stirred overnight at room temperature. The solution was then concentrated (30°/10$^{-4}$ mmHg) to give a viscous oil. $^1$H and $^{13}$C nmr (D$_2$O) showed complete conversion of the PAMAM 1.0 to the trisamide together with some maleic acid. $^{13}$C nmr (D$_2$O): δ 33.1, 42.8, 43.1, 54.3, 135.0, 137.1, 169.1, 171.9, 173.3.

The crude trisamide was then dissolved in water (4 ml) and solid sodium sulfite (0.20 g; 1.6 mmol) added. The resulting solution was allowed to stand at room temperature for four days and then concentrated. $^1$H and $^{13}$C nmr (D$_2$O) showed a 1:1 mixture of the regioisomeric sodium sulfosuccinamic acid terminated PAMAM 1.0 dendrimers together with some sulfosuccinic acid. The crude product was purified by gel filtration (Sephadex G10; water) to afford a sample of the sodium sulfosuccinamic acid terminated PAMAM 1.0 dendrimers (107 mg). $^{13}$C nmr (D$_2$O): δ 33.3, 39.6, 40.0, 42.9, 43.1, 54.0, 67.9, 69.4, 173.8, 176.3, 177.6, 181.8.

B. PAMAM 2.0

A mixture of the regioisomeric sodium sulfosuccinamic acid terminated PAMAM 2.0 dendrimers was prepared as described above. $^{13}$C nmr PAMAM 2.0 maleamic acid derivative (D$_2$O): δ 32.8, 33.0, 38.7, 42.9, 53.8, 54.3, 56.5, 135.2, 136.8, 169.2, 171.9, 173.5, 174.6. $^{13}$C nmr PAMAM 2.0 sodium sulfosuccinamic acid derivatives (D$_2$O): δ 37.0, 40.1, 41.1, 43.0, 43.2, 43.9, 53.0, 53.3, 55.5, 68.0, 69.4, 173.8, 177.6, 179.1, 179.5, 179.8, 182.3.

C. PAMAM 4.0 (Compound No. 14)

Solid maleic anhydride (60 mg; 0.6 mmol) was added to a stirred solution of PAMAM 4.0 (51 mg; 0.01 mmol) in dry DMF (2 ml). The mixture initially became cloudy but soon gave a clear solution which was stirred overnight at room temperature. The solution was then concentrated (35°/10$^{-4}$ mmHg) to give a viscous oil. $^1$H and $^{13}$C nmr (D$_2$O) showed complete conversion of the PAMAM 4.0 to the polyamide together with some maleic acid. The crude polyamide was then dissolved in water (2 ml) and a solution of sodium sulfite (126 mg; 1.0 mmol) in water (2 ml) added. The resulting solution was allowed to stand at room temperature for two days and then concentrated. $^1$H and $^{13}$C nmr (D$_2$O) showed a mixture of the regioisomeric sodium sulfosuccinamic acid terminated PAMAM 4.0 dendrimers together with some sulfosuccinic acid. The crude product was purified by gel filtration (Sephadex LH20; water) to afford a sample of PAMAM 4.0 terminated with 24 regioisomeric sulfosuccinamic acid groups (90 mg). $^1$H nmr (D$_2$O): δ 2.4–2.6; 2.7–3.1; 3.2–3.4; 3.9–4.0. $^{13}$C nmr (D$_2$O): δ 36.2; 39.8; 40.5; 43.0; 43.2; 53.5; 55.8; 68.1; 69.5; 173.8; 177.4; 177.6; 178.7; 182.3.

EXAMPLE 4

Preparation of sodium N-(2-sulfoethyl)succinamide terminated dendrimers a. Preparation of tetrabutylammonium N-(2-sulfoethyl) succinamic acid Solid succinic anhydride (0.50 g; 5.0 mmol) was added to a stirred solution of tetrabutylammonium 2-aminoethylsulfonic acid (1.83 g; 5.0 mmol) in dry dichloromethane (30 ml). The succinic anhydride slowly dissolved and the resulting cloudy solution was stirred overnight at room temperature. The mixture was filtered and the filtrate concentrated to give a viscous oil (2.41 g). $^{13}$C nmr showed complete conversion to the desired monoamide together with a small amount of succinic acid. Repeated precipitation of the product by dropwise addition of a dichloromethane solution to a large excess of diethyl ether gave tetrabutylammonium N-(2-sulfoethyl)succinamic acid as a white solid (1.762 g; 76% ), mp 125–127° C. 1 H nmr (CDCl$_3$): δ 0.86 (t, 12h, 4×CH$_3$), 1.28 (m, 8H, 4×CH$_2$), 1.50 (m, 8H, 4×CH$_2$), 2.33 (m, 2H, CH$_2$COOH), 2.44 (m, 2H, CH$_2$CONH), 2.76 (m, 2H, CH$_2$NHCO), 3.12 (m, 8H, 4×CH$_2$N), 3.50 (m, 2H, CH$_2$SO$_3^-$), 7.53 (br t, 1H, NH). $^{13}$C nmr (CDCl$_3$): δ 13.5, 19.5, 23.8, 30.1, 30.9, 35.6, 50.0, 58.5, 172.0, 174.1.

b. Preparation of tetrabutylammonium 4-nitrophenyl N-(2-sulfoethyl)-succinamate

A solution of dicyclohexylcarbodiimide (45 mg; 0.22 mmol) in dry dichloromethane (1 ml) was added to a stirred solution of tetrabutylammonium N-(2-sulfoethyl) succinamic acid (94 mg; 0.20 mmol) and 4-nitrophenol (28 mg; 0.20 mmol) in dichloromethane (2 ml), and the mixture stirred overnight at room temperature. The resulting suspension was filtered and the filtrate concentrated to give the crude active ester, which was used without further purification.

A. Preparation of sodium N-(2-sulfoethyl)succinamide terminated PAMAM dendrimers

PAMAM 4.0

A solution of the crude tetrabutylammonium 4-nitrophenyl N-(2-sulfoethyl)succinamate (0.30 mmol) in dry DMF (1 ml) was added to a stirred solution of PAMAM 4.0 (51.5 mg; 0.01 mmol) dissolved in 50% aqueous DMF (3 ml) and the resulting yellow solution stirred overnight at room temperature. The mixture was then concentrated (35°/10$^{-5}$ mmHg) and the yellow residue partitioned between water and chloroform. The water layer was separated, washed with chloroform (2×) and ethyl acetate, and then concentrated to give a yellow oil (134 mg). The crude product was converted to the sodium salt by passage through a column of Amberlite IR-120(Na) to yield 85 mg of material. This material was further purified by gel filtration (Sephadex LH20; water) to give the sodium N-(2-sulfoethyl) succinamide terminated PAMAM 4.0 dendrimer (45 mg). $^{13}$C nmr (D$_2$O): δ 33.2, 33.6, 35.5, 39.0, 39.5, 42.8, 43.2, 53.8, 54.1, 54.4, 56.6, 176.5, 176.9, 177.2, 178.9, 179.4.

The corresponding PAMAM 1.0 and PAMAM 3.0 dendrimers terminated with sodium N-(2-sulfoethyl) succinamide groups were similarly prepared. $^{13}$C nmr PAMAM 3.0 derivative (D$_2$O): δ 33.4, 35.5, 39.0, 39.5, 42.9, 43.2, 53.8, 54.1, 54.3, 56.5, 176.4, 176.9, 177.4, 178.9, 179.4.

$^{13}$C nmr PAMAM 1.0 derivative (D$_2$O): δ 34.9, 35.5, 39.5, 42.9, 43.1, 53.7, 54.1, 179.0, 179.1, 179.3.

B. Preparation of sodium N-(2-sulfoethyl)succinamide terminated polylysine dendrimers.

BHAlys$_2$lys$_4$lys$_8$lys$_{16}$

Trifluoroacetic acid (1 ml) was added to a suspension of BHAlys$_2$lys$_4$lys$_8$DBL$_{16}$ (36.5 mg; 5.0 μmol) in dry dichloromethane (1 ml) and the resulting solution stirred at room temperature under nitrogen for two hours and then concentrated. The residue was dissolved in dry DMSO (2 ml) and the pH adjusted to 8.5 with triethylamine. A solution of the crude tetrabutylammonium 4-nitrophenyl N-(2-sulfoethyl)succinamate (ca. 0.2 mmol) in DMSO (1 ml) was then added dropwise and the mixture stirred overnight at room temperature. The yellow solution was then concentrated (50°/10$^{-5}$ mmHg) and the yellow residue partitioned between water and chloroform. The aqueous layer was separated, washed with chloroform (3×) and ethyl acetate, and then concentrated to give an oil (99 mg). The crude product was converted to the sodium salt by passage through a column of Amberlite IR 120(Na) to yield 81 mg of material. This material was further purified by gel filtration (Sephadex LH20; water) to give the sodium N-(2-sulfoethyl)succinamide terminated BHAlyslys$_2$lys$_4$lys$_8$lys$_{16}$dendrimer (39 mg). $^{13}$C nmr (D$_2$O): δ 27.0, 32.3, 35.2, 35.3, 35.6, 35.7, 39.5, 43.5, 54.1, 58.5, 131.5, 132.0, 133.3, 145.1, 177.8, 178.0, 178.4, 178.8, 178.9, 179.2, 179.7, 179.8.

The corresponding BHAlyslys$_2$BHAlyslys$_2$lys$_4$ and BHAlyslys$_2$lys$_4$lys$_8$ terminated with sodium N-(2-sulfoethyl)succinamide groups were similarly prepared. $^{13}$C nmr BHAlyslys$_2$lys$_4$lys$_8$ derivative (D$_2$O): δ 26.9, 32.3, 35.1, 35.3, 35.6, 35.7, 39.5, 43.5, 54.1, 58.5, 131.6, 131.9, 132.2, 132.3, 133.2, 133.3, 145.0, 145.2, 177.2, 177.8, 177.9, 178.0, 178.2, 178.3, 178.6, 178.7, 178.8, 178.9, 179.2, 179.3, 179.7, 179.8.

$^{13}$C nmr BHAlyslys$_2$lys$_4$ derivative (D$_2$O): δ 26.9, 32.3, 35.1, 35.4, 35.7, 35.8, 39.5, 43.5, 54.1, 58.5, 61.8, 131.7, 132.0, 132.2, 132.3, 133.2, 133.3, 145.0, 145.1, 177.3, 178.0, 178.3, 178.4, 178.7, 178.9, 179.0, 179.3, 179.7, 179.8.

$^{13}$C nmr BHAlyslys$_2$ derivative (D$_2$O): δ 26.9, 27.1, 32.2, 32.3, 34.7, 34.8, 35.1, 35.3, 35.6, 35.7, 39.5, 43.4, 54.1, 58.6, 61.8, 131.7, 131.9, 132.2, 132.3, 133.3, 144.9, 145.0, 177.7, 178.4, 178.8, 179.0, 179.3, 180.0.

EXAMPLE 5
Preparation of sodium 4-sulfophenylthiourea terminated dendrimers
A. PAMAM 4.0 (Compound No. 1)

Solid sodium 4-sulfophenylisothiocyanate monohydrate (500 mg; 1.96 mmol) was added to a solution of PAMAM 4.0 (300 mg; 0.0582 mmol) in water (10 ml) and the resulting solution heated under nitrogen at 53° for two hours and then cooled. The solution was concentrated and the yellow solid residue purified by gel filtration (Sephadex LH20; water). The pure fractions were combined and freeze dried to give the sodium 4-sulfophenylthiourea terminated PAMAM 4.0 dendrimer as a fluffy white solid (370 mg). $^1$H nmr (D$_2$O): δ 2.28; 2.52; 2.69; 3.15; 3.27; 3.60; 7.32 (d, J=9 Hz); 7.72 (d, J=9 Hz). $^{13}$C nmr (D$_2$O): δ 36.9; 41.1; 43.1; 48.3; 53.6; 55.8; 129.0; 131.1; 144.4; 178.5; 179.1; 184.4.

The corresponding PAMAM 1.0 and PAMAM 2.0, PAMAM 3.0 and PAMAM 5.0 (Compound No. 2) dendrimers terminated with 3, 6, 12 and 48 sodium 4-sulfophenylthiourea groups respectively were similarly prepared.
B. PAMAM 4.0 (EDA) (Compound No. 3)

Solid sodium 4-sulfophenylisothiocyanate monohydrate (130 mg; 0.5 mmol) was added to a solution of PAMAM 4.0 (EDA) (69 mg; 0.01 mmol) in water (4 ml) and the resulting solution heated under nitrogen at 53° for two hours and then cooled. The solution was concentrated and the solid residue purified by gel filtration (Sephadex LH20; water). The pure fractions were combined and freeze dried to give PAMAM 4.0 terminated with 32 sodium 4-sulfophenylthiourea groups as a fluffy white solid (136 mg). $^1$H nmr (D$_2$O): δ 2.30; 2.50; 2.70; 3.18; 3.62; 7.35 (d, J=9 Hz); 7.72 (d, J=9 Hz). $^{13}$C nmr (D$_2$O): δ 36.8; 41.0; 43.1; 48.4; 53.6; 55.7; 128.9; 131.0; 144.3; 178.5; 179.0; 184.5.
C. BHAlyslys$_2$lys$_4$lys$_8$lys$_{16}$ (Compound No. 4)

Trifluoroacetic acid (4 ml) was added to a suspension of BHAlyslys$_2$lys$_4$lys$_8$DBL$_{16}$ (0.73 g; 0.1 mmol) in dry dichloromethane (4 ml) under nitrogen. A vigorous evolution of gas was observed for a short time and the resulting solution was stirred at room temperature for two hours and then concentrated. The residual syrup was dissolved in water (5 ml), the solution passed through a column of Amberlite IRA-401(OH) and the filtrate concentrated to give BHAlyslys$_2$lys$_4$lys$_8$lys$_{16}$ as a viscous oil (0.49 g). The oil was redissolved in water (5 ml) and N,N-dimethyl-N-allylamine buffer (pH 9.5; 3 ml) added. Solid sodium 4-sulfophenylisothiocyanate monohydrate (1.30 g; 5.1 mmol) was then added and the resulting solution heated under nitrogen at 53° for two hours and then cooled. The solution was concentrated and the brownish solid residue purified by gel filtration (Sephadex LH20; water). The pure fractions were combined, passed through a column of Amberlite IR 120(Na) and freeze dried to give the sodium 4-sulfophenylthiourea terminated BHAlyslys$_2$lys$_4$lys$_8$lys$_{16}$ dendrimer as a fluffy white solid (374 mg). $^1$H nmr (D$_2$O): δ 1.40; 1.72; 3.08; 3.42; 4.24; 4.60; 7.30; 7.40 (d, J=9 Hz); 7.78 (d, J=9 Hz). $^{13}$C nmr (D$_2$O): δ 27.3; 32.5; 35.9; 43.7; 48.9; 58.6; 63.3; 128.8; 131.0; 143.7; 144.7; 145.1; 177.7; 178.1; 183.8; 185.2.

The corresponding BHAlyslys$_2$lys$_4$lys$_8$, BHAlyslys$_2$lys$_4$lys$_8$lys$_{16}$lys$_{32}$ (Compound No. 5), and BHAlyslys$_2$lys$_4$lys$_8$lys$_{16}$lys$_{32}$lys$_{64}$ (Compound No. 6) dendrimers terminated with 16, 64, and 128 sodium 4-sulfophenylthiourea groups respectively were similarly prepared.

EXAMPLE 6
Preparation of sodium 3,6-disulfonapthylthiourea terminated dendrimers
A. PAMAM 4.0 (Compound No. 9)

Solid sodium 3,6-disulfonapthylisothiocyanate (160 mg; 0.41 mmol) was added to a solution of PAMAM 4.0 (51 mg; 0.01 mmol) in water (3 ml) and the resulting solution heated under nitrogen at 53° for two hours and then cooled. The solution was concentrated and the brown solid residue purified by gel filtration (Sephadex LH20; water). The pure fractions were combined and concentrated to give the sodium 3,6-disulfonapthylthiourea terminated PAMAM 4.0 dendrimer as a brownish solid (73 mg). $^1$H nmr (D$_2$O): δ 2.30; 2.60; 2.74; 3.20; 3.57; 7.75; 7.86; 8.28. $^{13}$C nmr (D$_2$O): δ 35.0; 39.9; 43.1; 48.1; 53.8; 56.1; 128.4; 128.6; 129.3; 131.0; 131.3; 136.0; 136.8; 138.2; 145.5; 146.0; 177.2; 177.8; 185.5.

The corresponding PAMAM 2.0 dendrimer terminated with sodium 3,6-disulfonapthylthiourea groups was similarly prepared.
B. PAMAM 4.0 (EDA) (Compound No. 11)

Solid sodium 3,6-disulfonapthylisothiocyanate (220 mg; 0.57 mmol) was added to a solution of PAMAM 4.0 (EDA) (74 mg; 0.01 mmol) in water (4 ml) and the resulting solution heated under nitrogen at 53° for two hours and then cooled. The solution was concentrated and the brownish solid residue purified by gel filtration (Sephadex LH20; water). The pure fractions were combined and concentrated to give PAMAM 4.0 terminated with 32 sodium 3,6-disulfonapthylthiourea groups as a tan solid (148 mg). $^1$H nmr (D$_2$O): δ 2.30; 2.80; 3.20; 3.54; 7.74; 7.85; 8.25. $^{13}$C nmr (D$_2$O): δ 36.0; 40.8; 43.1; 48.3; 53.6; 5.9; 128.5; 129.4; 131.0; 131.3; 136.0; 136.8; 138.3; 145.5; 146.0; 178.2; 185.6.

C. BHAlyslys$_2$lys$_4$lys$_8$lys$_{16}$ (Compound No. 12)

Trifluoroacetic acid (2 ml) was added to a suspension of BHAlyslys$_2$lys$_4$lys$_8$DBL$_{16}$ (73 mg; 0.01 mmol) in dry dichloromethane (2 ml) under nitrogen A vigorous evolution of gas was observed for a short time and the resulting solution was stirred at room temperature for two hours and then concentrated. The residual syrup was dissolved in water (5 ml), the solution passed through a column of Amberlite IRA-401 (OH) and the filtrate concentrated to give BHAlyslys$_2$lys$_4$lys$_8$lys$_{16}$ as a viscous oil. The oil was redissolved in water (5 ml) and N,N-dimethyl-N-allylamine buffer (pH 9.5; 3 ml) added. Solid sodium 3,6-disulfonapthylisothiocyanate (234 mg; 0.60 mmol) was then added and the resulting solution heated under nitrogen at 53° for two hours and then cooled. The solution was concentrated and the brownish solid residue purified by gel filtration (Sephadex LH20; water). The pure fractions were combined, passed through a column of Amberlite IR 120 (Na) and freeze dried to give BHAlyslys$_2$lys$_4$lys$_8$lys$_{16}$ terminated with 32 sodium 3,6-disulfonapthylthiourea groups as a fluffy off-white solid (119 mg). $^1$H nmr (D$_2$O): δ 1.0–2.0; 3.18; 3.43; 4.31; 7.22; 7.80; 7.89; 8.25. $^{13}$C nmr (D$_2$O): δ 27.2; 32.4; 35.3; 43.7; 49.0; 58.5; 63.6; 128.4; 129.1; 131.4; 136.1; 136.6; 138.6; 139.0; 145.1; 145.6; 178.4; 184.8; 186.7.

EXAMPLE 7

Preparation of sodium 4-sulfonapthylthiourea terminated dendrimers

PAMAM 4.0 (Compound No. 8)

Solid sodium 4-sulfonapthylisothiocyanate (180 mg; 0.5 mmol) was added to a solution of PAMAM 4.0 (51 mg; 0.01 mmol) in water (5 ml) and the mixture heated under nitrogen at 530 for two hours and then cooled. The water was distilled under reduced pressure from the resulting suspension and the off white solid residue purified by gel filtration (Sephadex LH20; water). The pure fractions were combined and freeze dried to give the sodium 4-sulfonapthylthiourea terminated PAMAM 4.0 dendrimer as a fluffy white solid (60 mg). $^1$H nmr (D$_2$O): δ 2.20; 2.60; 3.14; 3.48; 7.23; 7.47; 7.56; 7.77; 7.93 (d, J=6 Hz); 8.56 (d, J=6 Hz). $^{13}$C nmr (D$_2$O): δ 35.8; 40.5; 43.1; 48.4; 53.6; 55.9; 127.6; 128.6; 130.3; 131.9; 132.5; 133.5; 134.7; 140.5; 142.7; 177.8; 178.0; 185.4.

EXAMPLE 8

Preparation of sodium 3,5-disulfophenylthiourea terminated dendrimers

PAMAM 4.0 (Compound No. 7)

Solid sodium 3,5-disulfophenylisothiocyanate (110 mg; 0.32 mmol) was added to a solution of PAMAM 4.0 (63 mg; 0.012 mmol) in water (3 ml) and the resulting solution heated under nitrogen at 53° for two hours and then cooled. The solution was concentrated and the brownish solid residue purified by gel filtration (Sephadex G25; water). The pure fractions were combined and concentrated to give PAMAM 4.0 terminated with 24 sodium 3,5-disulfophenylthiourea groups as an off-white solid (110 mg). $^1$H nmr (D$_2$O): δ 2.53; 3.08; 3.36; 3.66; 7.90; 7.95. $^{13}$C nmr (D$_2$O): δ 34.8; 41.0; 43.1; 48.0; 53.7; 56.2; 124.1; 128.6; 143.5; 148.8; 177.6; 185.0.

EXAMPLE 9

Preparation of sodium 3, 6, 8-trisulfonaphthylthiourea terminated dendrimers

PAMAM 4.0 (Compound No. 10)

Solid sodium 3, 6, 8-trisulfonaphthylisothiocyanate (250 mg; 0.5 mmol) was added to a solution of PAMAM 4.0 (51 mg; 0.01 mmol) and N,N-dimethyl-N-allylamine buffer (pH 9.5; 1 ml) in water (2 ml) and the mixture heated under nitrogen at 53° for two hours and then cooled. The mixture was concentrated under reduced pressure to give an orange solid. The residual solid was dissolved in water (2 ml) and passed through a short column of Amberlite IR-120(Na). The filtrate was then concentrated and the residue purified by gel filtration (Sephadex LH20; water). The pure fractions were combined and freeze dried to give the sodium 3, 6, 8-trisulfonaphthylthiourea terminated PAMAM 4.0 dendrimer as an off-white solid (102 mg). $^1$H nmr (D$_2$O): δ 2.65; 3.02; 3.30; 3.66; 8.05; 8.42; 8.59; 8.67. $^{13}$C nmr (D$_2$O): δ 33.2; 38.7; 43.2; 43.7; 47.8; 54.0; 54.3; 56.7; 131.0; 131.3; 131.9; 135.9; 138.0; 139.6; 143.8; 144.1; 145.6; 176.2; 176.5; 186.0.

EXAMPLE 10

Preparation of sodium 4-(sulfomethyl)benzamide terminated dendrimers

PAMAM 4.0 (Compound No. 13)

Solid 4-nitrophenyl 4-(chloromethyl)benzoate (200 mg; 0.68 mmol) was added to a stirred solution of PAMAM 4.0 (70 mg; 0.014 mmol) in dry DMSO (4 ml) and the resulting yellow solution stirred at room temperature for two hours. The solution was then concentrated ($10^{-4}$ mmHg; 40°) and the residue extracted with a mixture of water and dichloromethane (1:1). The remaining solid material was dissolved in DMSO (5 ml) and a solution of sodium sulfite (130 mg; 1 mmol) in water (3 ml) added. The slightly cloudy mixture that resulted was left to stand for four days, after which time the addition of more water (2 ml) resulted in the formation of a clear homogeneous yellow solution. The solution was then concentrated, first at 25 mmHg and 40 then at 10 mmHg and 50 to give the crude product. The crude product was purified by gel filtration (Sephadex G25; water) to give PAMAM 4.0 terminated with 24 sodium 4-(sulfomethyl) benzamide groups (24 mg). $^1$H nmr (D$_2$O): δ 2.25; 2.66; 3.08; 3.20; 3.33; 3.38; 4.01; 7.40 (br d); 7.62 (br d). $^{13}$C nmr (D$_2$O): δ 36.7; 40.9; 43.0; 43.6; 53.5; 55.5; 61.0; 131.6; 135.0; 137.2; 140.4; 174.5; 178.6; 179.2.

EXAMPLE 11

Preparation of 4-sulfobenzamide terminated dendrimers

PAMAM 4.0 (EDA)

Solid potassium N-hydroxysuccinimidyl 4-sulfobenzoate (100 mg; 0.3 mmol) was added to a solution of PAMAM 4.0 (EDA) (35 mg; 0.005 mmol) in 0.1 M pH 8.5 borate buffer (5 ml) and the solution stirred at room temperature for two hours. The resulting milky solution at this stage had a pH of 4.5. 1M Sodium carbonate solution (1 ml) was then added to give a clear solution which was concentrated to give the crude product as a white solid. The crude product was purified by gel filtration (Sephadex G25; water) to give PAMAM 4.0 EDA terminated with 32 sodium 4-sulfobenzamide groups (47 mg). $^1$H nmr (D$_2$O) δ 2.25; 2.42; 2.63; 3.05; 3.18; 3.31; 3.38; 7.72 (d, s=8 Hz); 7.78 (d, 3=8 Hz). $^{13}$C nmr (D$_2$O): δ 36.0; 40.4; 43.0; 43.7; 53.7; 55.8; 130.2; 132.2; 140.4; 150.1; 173.6; 178.0; 178.5.

EXAMPLE 12

Preparation of Sodium N-(4-sulfophenyl)propanamide terminated dendrimers

PAMAM 4.0 (EDA)

Solid sodium N-(4-sulfophenyl)acrylamide (250 mg; 1 mmol) and solid sodium carbonate (106 mg; 1 mmol) were added successively to a stirred solution of PAMAM 4.0 (EDA) (78 mg; 0.011 mmol) in water (4 ml). The resulting solution was stirred under nitrogen for four days and then freeze dried to give a fluffy white solid. The crude product was purified by gel filtration (Sephadex LH20; water to give PAMAM 4.0 (EDA) terminated with 64 sodium N-(4-sulfophenyl)propanamide groups (206 mg). $^{13}$C nmr showed a faint trace of what was taken to be mono alkylated terminal amino groups. $^{1}$H nmr (D$_2$O):δ 2.10; 2.48; 2.58; 2.79; 3.20; 7.42 (d, J=7 Hz); 7.65 (d, J=7 Hz). $^{13}$C nmr (D$_2$O): δ 36.5; 37.9; 41.1; 53.4; 55.6; 124.8; 130.9; 143.0; 144.2; 177.4; 178.5.

EXAMPLE 13

Preparation of Sodium 4-sulfophenylurea terminated dendrimers

PAMAM 4.0 (EDA)

A solution of sodium sulfanilic acid (195 mg; 1 mmol) in dry DMSO (3 ml) was added dropwise to a solution of N,N'-disuccinimidyl carbonate (530 mg; 2 mmol) in dry DMSO (4 ml) and the resulting brownish solution stirred at room temperature for 20 hours. A solution of PAMAM 4.0 (EDA) (75 mg; 0.011 mmol) in dry DMSO (1 ml) added and the solution stirred for a further 18 hours. The solution was then concentrated under high vacuum ($10^{-5}$ mmHg; 35°) to give a yellowish semi solid. The crude product was dissolved in DMSO (4 ml) and the solution added to 200 ml of well stirred ethyl acetate. The precipitated white solid was collected by filtration and washed with ethyl acetate (2×) and ether (2×), then dried to give a white powder (275 mg). This material was further purified by gel filtration (Sephadex LH20; water) to give PAMAM 4.0 (EDA) terminated with 32 sodium 4-sulfophenylurea groups (106 mg). $^{1}$H nmr (D$_2$O): 62.31; 2.55; 2.75; 3.19; 7.32 (d, J=9 Hz); 7.63 (d, J=9 Hz). $^{13}$C nmr (D$_2$O): δ 36.3; 40.7; 43.3; 43.8; 53.7; 55.7; 123.3; 130.9; 140.9; 146.0; 161.4; 178.2; 178.6.

EXAMPLE 14

Preparation of N,N,N-trimethylglycinamide chloride terminated dendrimers.

BHAlyslys$_2$lys$_4$lys$_8$lys$_{16}$ (Compound No. 15)

Trifluoroacetic acid (4 ml) was added to a suspension of BHAlyslys$_2$lys$_4$lys$_8$DBL$_{16}$ (220 mg; 30 μmol) in dry dichloromethane (2 ml) and the resulting solution stirred at room temperature under nitrogen for two hours and then concentrated. The residue was dissolved in dry DMSO (5 ml) and the pH adjusted to 8.5 with triethylamine. Solid 4-nitrophenyl N,N,N-trimethylglycinate chloride (0.50 g; 1.8 mmol) was then added and the mixture stirred overnight at room temperature. The cloudy solution was then concentrated (50°/$10^{-5}$ mmHg) and the residue partitioned between water and dichloromethane. The aqueous layer was separated, washed with dichloromethane (3×) and ethyl acetate, and then concentrated to give an oil (1.128 g). The crude product was purified by gel filtration (Sephadex LH20; water) to give the N,N,N-trimethylglycinamide terminated BHAlyslys$_2$lys$_4$lys$_8$lys$_{16}$ dendrimer (116 mg). $^{13}$C nmr (D$_2$O): δ 25.5, 30.5, 30.8, 33.4, 42.1, 56.5, 57.1, 67.5, 68.1, 166.7, 167.0, 167.1, 176.0, 176.2.

EXAMPLE 15

Preparation of 4-Trimethylammoniumbenzamide terminated dendrimers

PAMAM 4.0 (Compound No. 16)

1,1'-Carbonyldiimidazole (85 mg; 0.52 mmol) was added to a solution of 4-trimethylammoniumbenzoic acid iodide (154 mg; 0.5 mmol) in dry DMF (4 ml) and the mixture stirred at room temperature under argon for two hours. During this time a white solid separated from the solution. A solution of PAMAM 4.0 (58 mg; 0.011 mmol) in dry DMF (2 ml) was then added and the mixture stirred overnight at room temperature. After this time most of the precipitate had dissolved and a ninhydrin test of the solution was negative. The mixture was concentrated (10 mmHg; 30°) to give a white solid residue. The crude product was purified by gel filtration (Sephadex LH20; 10% AcOH) to give PAMAM 4.0 terminated with 24 4-trimethylammoniumbenzamide groups as the acetic acid salt (89 mg). $^{1}$H nmr (D$_2$O): δ 1.96; 2.65–2.85; 3.25–3.55; 3.64; 7.92. $^{13}$C nmr (D$_2$O): δ 25.8; 33.1; 33.5; 38.7; 43.1; 43.5; 53.5; 54.1; 56.4; 61.2; 124.8; 133.6; 139.9; 153.2; 173.2; 176.3; 176.8; 182.6.

The corresponding PAMAM 2.0 dendrimer terminated with 6 4-trimethylammonium benzamide groups was similarly prepared.

EXAMPLE 16

Preparation of 4-(Trimethylammoniummethyl)benzamide terminated dendrimers

PAMAM 4.0 (Compound No. 17)

Solid 4-nitrophenyl 4-(chloromethyl)benzoate (150 mg; 0.5 mmol) was added to a stirred solution of PAMAM 4.0 (52 mg; 0.01 mmol) in dry DMSO (3 ml). The resulting yellow solution was stirred at room temperature for 20 hours, when a ninhydrin test was negative (pH ca.8.5). The solution was then concentrated (10 mmHg; 40 ) and the residue shaken with a mixture of water and dichloromethane (1:1). The insoluble gel-like material was collected by filtration, washed with water (2×) and dichloromethane (2×), and then air dried. The crude 4-(chloromethyl)benzamide terminated dendrimer was dissolved in 25% aq. trimethylamine (20 ml) and the yellow solution left to stand overnight. The solution was then concentrated, the residue dissolved in water (5 ml) and the solution passed through a column of Amberlite IRA-401 (OH). The colourless filtrate was concentrated to give a viscous oil which was purified by gel filtration (Sephadex G10; 10% AcOH) to give PAMAM 4.0 terminated with 24 4-(trimethylammoniummethyl) benzamide groups (90 mg). $^{1}$H nmr (D$_2$O): δ 1.88; 2.65–2.80; 2.98; 3.10–3.60; 7.52 (br d, J=9 Hz); 7.72 (br d, J=9 Hz). $^{13}$C nmr (D$_2$O): δ 26.6; 33.4; 38.8; 43.2; 43.5; 53.6; 53.6; 54.1; 56.8; 62.8; 73.0; 132.1; 135.3; 137.5; 140.0; 176.4; 176.9; 183.6.

EXAMPLE 17

Preparation of N-(2-Acetoxyethyl)-N,N-(dimethylammonium)methylcarboxamide terminated dendrimers

PAMAM 4.0

Solid 1,1'-carbonyldiimidazole (85 mg; 0.52 mmol) was added to a solution of N-(2-acetoxyethyl)-N-(carboxymethyl)-N,N-dimethylammonium bromide (135 mg; 0.5 mmol) in dry DMF (3 ml) and the resulting solution stirred under nitrogen for two hours. A solution of PAMAM 4.0 (60 mg; 0.012 mmol) in DMF (2 ml) was then added, which caused the immediate formation of a flocculant precipitate which slowly redissolved. The mixture was stirred for two days and then concentrated ($10^{-4}$ mmHg; 40°) to give a viscous oil. The crude product was purified by gel filtration (Sephadex G10; 10% AcOH) to give PAMAM 4.0 terminated with 24 N-(2-Acetoxyethyl)-N,N-(dimethylammonium)methylcarboxamide groups (64 mg). $^{1}$H nmr (D$_2$O): δ 1.93; 2.05; 2.70; 3.10–3.60; 3.28; 3.93 (m); 4.14; 4.48 (m). $^{13}$C nmr (D$_2$O): δ 24.6; 26.2; 33.2; 38.7; 42.8; 42.9; 53.9; 57.4; 62.6; 67.3; 67.5; 168.9; 176.4; 176.8; 177.3; 183.2.

EXAMPLE 18
Preparation of Guanidino terminated dendrimers
PAMAM 4.0 (Compound No. 18)

A solution of PAMAM 4.0 (63 mg; 0.012 mmol) and methylthiopseudourea sulfate (170 mg; 0.61 mmol) in water (5 ml) (pH 10.5) was heated under nitrogen at 80° for two hours. The solution was then concentrated and the residue purified by gel filtration (Sephadex G10; 10% AcOH) to give PAMAM 4.0 terminated with 24 guanidino groups as the acetate salt (107 mg). $^1$H nmr (D$_2$O): δ 2.00; 2.80 (br t); 3.09 (br t); 3.32; 3.45 (br t); 3.60 (br t). $^{13}$C nmr (D$_2$O): δ 25.2; 33.2; 33.4; 38.7; 41.2; 42.6; 43.4; 44.7; 53.5; 54.0; 56.3; 176.5; 176.7; 176.9; 181.6.

The corresponding PAMAM 2.0 dendrimer terminated with 6 guanidino groups was similarly prepared.

EXAMPLE 19
Preparation of 4-([1,4,8,11-tetraazacyclotetradecane]methyl)benzamide terminated dendrimers
PAMAM 4.0 (Compound No. 19)

A solution of 1-(4-carboxyphenyl)methyl-1,4,8,11-tetraaacyclotetradecane tetra hydrochloride (120 mg; 0.25 mmol), N-hydroxysuccinimide (60 mg; 0.52 mmol) and 1-(3-dimethylaminopropyl)-3-ethylcarbodiimide hydrochloride (250 mg; 1.3 mmol) in pH 7 phosphate buffer (10 ml) was allowed to stand a room temperature for one hour and then a solution of PAMAM 4.0 (32 mg; 0.006 mmol) in pH 7 phosphate buffer (10 ml) added. The mixture was allowed to stand for two days and then concentrated. The residue was purified by gel filtration (Sephadex LH20; 10% AcOH) to give PAMAM 4.0 terminated with ca 12 4-([1,4,8,11-tetraaacyclotetradecane]methyl)benzamide groups as determined by $^1$H and $^{13}$C nmr (80 mg). The product was then dissolved in water and passed through a column of Amberlite IRA-401 (Cl) resin and then concentrated. The residue was dissolved in water (1 ml), concentrated HCl (1 ml) added, and the solution diluted with ethanol (30 ml) to precipitate a white solid. The solid was collected by filtration (68 mg). Once again $^1$H and $^{13}$C nmr showed ca. 50% functionalisation of the terminal amino groups. $^1$H nmr (D$_2$O): δ 2.17; 2.36; 2.50; 2.78; 2.85; 3.25; 3.40; 3.50; 3.60; 3.62; 4.49; 7.63 (br d); 7.78 (br d). $^{13}$C nmr (D$_2$O): δ 22.7; 23.1; 33.2; 38.8; 39.9; 40.2; 40.3; 41.0; 41.2; 42.0; 42.9; 43.2; 43.6; 45.5; 46.1; 49.1; 52.2; 53.9; 54.3; 56.6; 62.7; 132.5; 135.7; 137.1; 139.7; 174.3; 176.2; 176.3; 176.7; 177.0; 178.2; 178.5.

EXAMPLE 20
Preparation of 4-Carboxy-3-hydroxybenzylamine terminated dendrimers
PAMAM 4.0 (EDA)

Sodium cyanoborohydride (32 mg; 0.5 mmol) was added to a mixture of PAMAM 4.0 (EDA) (69 mg; 0.01 mmol), 4-formyl-2-hydroxybenzoic acid (83 mg; 0.5 mmol), and sodium hydrogen carbonate (42 mg; 0.5 mmol) in water (4 ml). The inhomogeneous orange mixture was stirred for four hours at room temperature, during which time it became homogeneous. The orange solution was then concentrated and the residue purified by gel filtration (Sephadex LH20; water) to give PAMAM 4.0 (EDA) terminated with ca. 32 4-carboxy-3-hydroxybenzylamine groups (91 mg). $^1$H and $^{13}$C nmr (D$_2$O) shows mostly mono alkylation but with some signs of dialkylation of the terminal amino groups, both spectra show broad peaks. $^{13}$C nmr (D$_2$O): δ 37.0; 41.1; 50.9; 53.4; 55.5; 55.8; 61.5; 120.9; 122.2; 122.4; 132.3; 132.7; 135.0; 135.8; 163.5; 163.7; 169.0; 178.6; 179.3. $^1$H nmr (D$_2$O): δ 2.20; 2.35; 2.60; 3.15; 3.30; 3.55; 4.25; 6.68; 7.12; 7.55.

EXAMPLE 21
Test for anticoagulant activity

Bovine blood was collected from the abattoir, where an animal was bled into a bucket containing sodium citrate at a concentration of 3.5 g per liter of fresh blood. This blood was returned to the laboratory where it was kept in a 37° C. water bath.

Aliquots of the whole blood were then centrifuged at 3000 rpm for 5 minutes to separate the plasma This was collected and returned to the water bath. Extra plasma was also prepared and stored in liquid nitrogen for later testing.

The procedure actually tests the recalcification time of the citrated blood at 37° C. All glassware was washed, dried and silated with 'Coatasil' before re-washing and drying. Each 12×75 mm culture tube contained 0.1 ml of plasma, 0.1 ml of saline solution (0.9% NaCl) followed by 0.1 ml of 0.025M CaCl$_2$ at which time the stop watch was started. Every 15 sec the tube was tilted to one side and clotting was assessed. When a firm clot had formed, the watch was stopped and the time recorded. In the case of testing anticoagulants 0.1 ml of the test substance replaced the saline. The times for a range of concentrations for the test compounds are recorded in Table 1. Heparin, sodium citrate and test compound were made up in water as 10 mg/ml solutions. These solutions were diluted to give a range of concentrations. The final concentrations in the test tubes are given in the table. The figures in the table represent average times for, up to ten replicates.

TABLE 1

| | Time for plasma coagulation at 37° C. for following concentrations of anticoagulant | | | | | |
|---|---|---|---|---|---|---|
| Compound | Controls | 0.0003 mg/ml | 0.003 mg/ml | 0.03 mg/ml | 0.33 mg/ml | 3.33 mg/ml |
| Heparin | 2.29 min | 2.30 min | >30 min | >30 min | >30 min | — |
| Sodium citrate | 2.29 min | — | — | 2.30 min | 2.30 min | >30 min |
| Compound No. 1 | 2.11 min | — | — | 2.29 min | 4.00 min | >30 min |
| Compound No. 4 | 2.08 min | — | — | 1.72 min | 10.00 min* | >30 min |
| Compound No. 15 | 2.20 min | — | 2.34 min | 7 min* | 8 min* | — |
| Compound No. 9 | 2.27 min | — | 2.19 min | 4 min | 5.40 min* | — |

EXAMPLE 23
Test for antiviral activity.

The results of tests of activity against HIV1, HIV2, CMV and various herpes simplex viruses (HSV) are recorded in Tables 2 to 5, respectively.

TABLE 2
HIV 1 Activity Results
| Dendrimer | Terminal Group | EC$_{50}$ μM | CC$_{50}$ μM | Antiviral Index |
|---|---|---|---|---|
| (1) PAMAM 4.0<br>24 end groups | 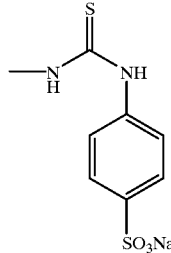 | 0.0492 | >125 | >2543 |
| (2) PAMAM 5.0<br>48 end groups | 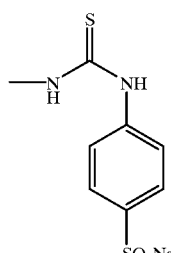 | 0.0096 | >11 | >1180 |
| (3) PAMAM 4.0 (EDA)<br>32 end groups | 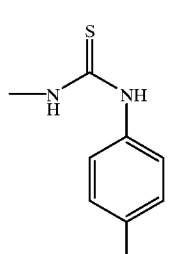 | 0.0142 | >17.2 | >1212 |
| (4) BHAlys$_{15}$lys$_{16}$<br>32 end groups | 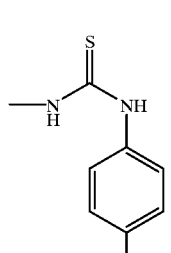 | 0.0126 | 100.91 | 7991 |
| (5) BHAlys$_{31}$lys$_{32}$<br>64 end groups | 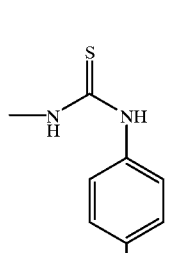 | 0.0332 | >10 | >320 |

TABLE 2-continued

HIV 1 Activity Results

| Dendrimer | Terminal Group | EC$_{50}$ µM | CC$_{50}$ µM | Antiviral Index |
|---|---|---|---|---|
| (6) BHAlys$_{63}$lys$_{64}$ 128 end groups | 4-sulfophenyl thiourea (–NH-CS-NH-C$_6$H$_4$-SO$_3$Na) | 0.0530 | >5 | >100 |
| (7) PAMAM 4.0 24 end groups | 3,5-disulfophenyl thiourea | 0.003 | >18.8 | >9091 |
| (8) PAMAM 4.0 24 end groups | 4-sulfonaphthyl thiourea | 0.0694 | >20 | >300 |
| (9) PAMAM 4.0 24 end groups | disulfonaphthyl thiourea | 0.0032 | >125 | >39000 |
| (10) PAMAM 4.0 24 end groups | trisulfonaphthyl thiourea | 0.0041 | >14 | >3500 |
| (11) PAMAM 4.0 (EDA) 32 end groups | disulfonaphthyl thiourea | 0.0051 | >12.9 | >2537 |

TABLE 2-continued

HIV 1 Activity Results

| Dendrimer | Terminal Group | EC$_{50}$ μM | CC$_{50}$ μM | Antiviral Index |
|---|---|---|---|---|
| (12) BHAlys$_{15}$lys$_{16}$ 32 end groups | [thiourea-linked naphthalene with two SO$_3$Na groups] | 0.0088 | >15 | >1700 |
| (13) PAMAM 4.0 24 end groups | [benzamide with CH$_2$SO$_3$Na] | 0.0088 | >24 | >2737 |
| (14) PAMAM 4.0 24 end groups | HOOC–C(NaO$_3$S)–CH$_2$–C(O)NH– | 0.2849 | >25 | >88 |
| (15) BHAlys$_{15}$lys$_{16}$ 32 end groups | Me$_3$N$^+$CH$_2$CONH— | 0.0725 | >125 | >1720 |
| (16) PAMAM 4.0 24 end groups | [4-(NMe$_3^+$)benzamide] CONH– | 1.2559 | >25 | >20 |
| (17) PAMAM 4.0 24 end groups | [4-(CH$_2$NMe$_3^+$)benzamide] CONH– | 0.2973 | 2.3406 | 8 |
| (18) PAMAM 4.0 24 end groups | [guanidino group] –NH–C(=NH)NH$_2$ | 0.2739 | 3.4983 | 13 |
| (19) PAMAM 4.0 ca. 12 end groups | [cyclam-CH$_2$-phenyl-CONH–] | 0.0538 | 3.2183 | 60 |

TABLE 3
HIV 2 Activity Results
| Dendrimer | Terminal Group | EC$_{50}$ μM | CC$_{50}$ μM | Antiviral Index |
|---|---|---|---|---|
| (1) PAMAM 4.0<br>24 end groups | 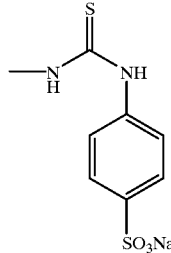 | 0.2237 | >125 | >560 |
| (2) PAMAM 5.0<br>48 end groups | 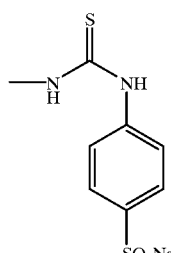 | 0.1490 | >11 | >76 |
| (3) PAMAM 4.0 (EDA)<br>32 end groups | 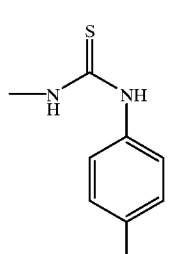 | 0.2368 | >17.2 | >73 |
| (4) BHAlys$_{15}$lys$_{16}$<br>32 end groups | 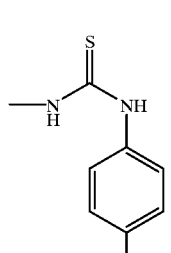 | 0.1130 | 108.0417 | 956 |
| (5) BHAlys$_{31}$lys$_{32}$<br>64 end groups | 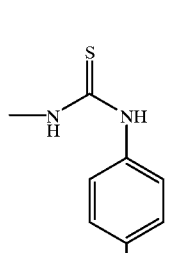 | 0.2063 | >10 | >52 |

TABLE 3-continued

HIV 2 Activity Results

| Dendrimer | Terminal Group | EC$_{50}$ μM | CC$_{50}$ μM | Antiviral Index |
|---|---|---|---|---|
| (6) BHAlys$_{63}$lys$_{64}$ 128 end groups | −NH−C(=S)−NH−C$_6$H$_4$−SO$_3$Na | 0.2227 | >5 | >24 |
| (7) PAMAM 4.0 24 end groups | −NH−C(=S)−NH−C$_6$H$_3$(SO$_3$Na)$_2$ (3,5-disulfo) | 0.24 | >18.8 | >77 |
| (8) PAMAM 4.0 24 end groups | −NH−C(=S)−NH−(naphthyl)−SO$_3$Na (1,4) | 0.4913 | >20 | >42 |
| (9) PAMAM 4.0 24 end groups | −NH−C(=S)−NH−(naphthyl)(SO$_3$Na)$_2$ | 0.0674 | >125 | >1854 |
| (10) PAMAM 4.0 24 end groups | −NH−C(=S)−NH−(naphthyl)(SO$_3$Na)$_3$ | 0.0299 | >14 | >493 |
| (11) PAMAM 4.0 (EDA) 32 end groups | −NH−C(=S)−NH−(naphthyl)(SO$_3$Na)$_2$ | 0.0234 | >12.9 | >551 |

TABLE 3-continued

HIV 2 Activity Results

| Dendrimer | Terminal Group | EC$_{50}$ μM | CC$_{50}$ μM | Antiviral Index |
|---|---|---|---|---|
| (12) BHAlys$_{15}$lys$_{16}$ 32 end groups | [thiourea-linked naphthalene-disulfonate, NaO$_3$S and SO$_3$Na substituents] | 0.1778 | >15 | >85 |
| (13) PAMAM 4.0 24 end groups | [benzamide with CH$_2$SO$_3$Na] | 0.1080 | >24 | >222 |
| (14) PAMAM 4.0 24 end groups | [HOOC-C(NaO$_3$S)-CH$_2$-CONH-] | 6.002 | >25 | >4 |
| (15) BHAlys$_{15}$lys$_{16}$ 32 end groups | Me$_3$N$^+$CH$_2$CONH— | >125 | >125 | |
| (16) PAMAM 4.0 24 end groups | [4-(+NMe$_3$)benzamide, CONH-] | >25 | >25 | |
| (17) PANAM 4.0 24 end groups | [4-(CH$_2$+NMe$_3$)benzamide, CONH-] | >7.175 | >7.175 | <1 |
| (18) PAMAM 4.0 24 end groups | [guanidine, -NH-C(=NH)-NH$_2$] | >10.817 | 10.817 | <1 |
| (19) PAMAM 4.0 ca. 12 end groups | [cyclam-CH$_2$-C$_6$H$_4$-CONH—] | 0.2175 | 2.4245 | 11 |

TABLE 4

Activity against Human Cytomegalovirus
Cell culture (Davis strain)

| Compound | EC$_{50}$ ($\mu$g/ml) | CC$_{50}$ ($\mu$g/ml) |
| --- | --- | --- |
| Compound No. 15 | 1.0 | ≧250 |
| Compound No. 9 | 0.2 –< 0.4 | ≧250 |

Tests in human embrionic lung cells (HEL).
IC$_{50}$ = Inhibitory concentration to reduce virus plaque by 50%
CC$_{50}$ = Cytotoxic concentration required to reduce HEL cell growth by 50%

TABLE 5

Activity of BRI compounds against miscellaneous viruses.

| Compound | Minimum Cytotoxic Concentration[a] ($\mu$g/ml) | Herpes simplex virus-1 (KOS) | Herpes simplex virus-2 (G) | Herpes simplex virus-1 TK-B2006 | Herpes Simplex virus-1 TK-VMW1837 |
| --- | --- | --- | --- | --- | --- |
| | | Minimum Inhibitory Concentration[b] ($\mu$g/ml) | | | |
| Compound No. 4 | ≧400 | 70 | 7 | 150 | 70 |
| Compound No. 20 | ≧400 | 7 | 20 | 20 | 20 |

[a]Required to cause a microscopically detectable alteration of normal morphology.
[b]Required to reduce virus-induced cytopathogenicity by 50%.

We claim:

1. A composition (A) that displays antiviral activity in an in vitro assay and (B) that comprises an dendrimer having a plurality of terminal groups wherein at least one of said terminal groups has an anionic or cationic moiety, other than a 2-thiosialic acid moiety, bonded thereto.

2. A composition according to claim 1, wherein said dendrimer, comprises a polyvalent core covalently bonded to at least two dendritic branches, and extends through at least two generations.

3. A composition according to claim 1, wherein said dendrimer is a polyamidoamine dendrimer based on an ammonia core.

4. A composition according to claim 1, wherein said dendrimer is a polyamidoamine dendrimer based on an ethylene diamine core.

5. A composition according to claim 1, wherein said dendrimer is a polylysine dendrimer based on a benzhydrylamine or other suitable core.

6. A composition according to claim 1 wherein at least one of said anionic- or cationic-containing moieties is bonded to terminal amine, sulfhydryl, hydroxy or other reactive functional terminal group of said dendrimer by amide or thiourea linkages.

7. A composition according to claim 1 wherein at least one of said anionic-containing moieties is a sulfonic acid-containing moiety or carboxylic acid-containing moiety.

8. A composition according to claim 1 wherein at least one of said cationic-containing moieties is a trimethylammonium-containing moiety or polyaminomacrocyclic-containing moiety.

9. A composition to claim 1 wherein at least one of the moieties which are bonded to amino or other reactive functional terminal groups of the dendrimer is selected from the group Ar(COO—)$_n$ consisting of —NH(CH$_2$)$_n$SO$_3^-$—(CH$_2$)$_n$SO$_3^-$—Ar(SO$_3^-$)$_n$ —CH$_2$CH(SO$_3^-$)COOH—CH(SO$_3^-$)CH$_2$COOH—ArX(CH$_2$)$_n$SO$_3^-$
X=O, S, NH —(CH$_2$)$_n^+$NMe$_3$—Ar(N$^+$Me$_3$)$_n$—Ar(CH$_2$N$^+$Me$_3$)$_n$

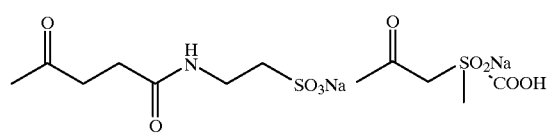

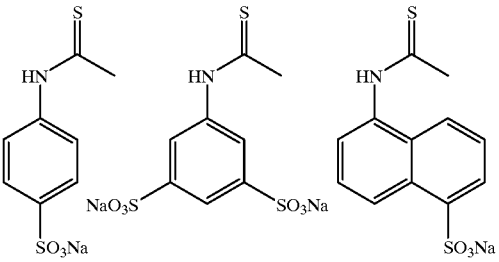

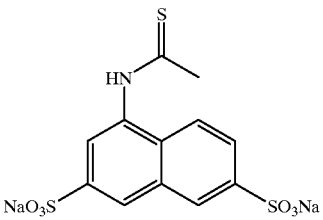

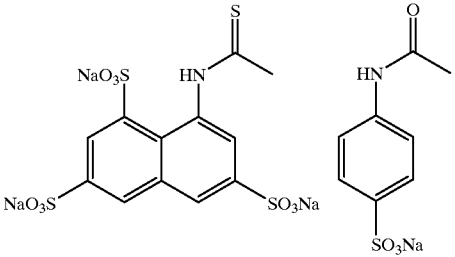

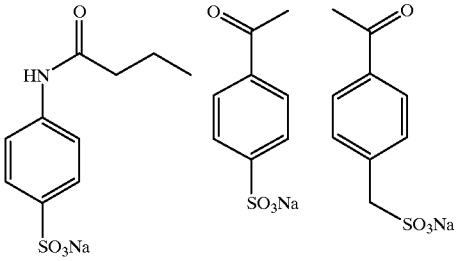

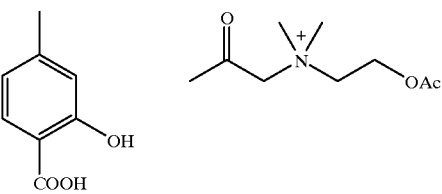

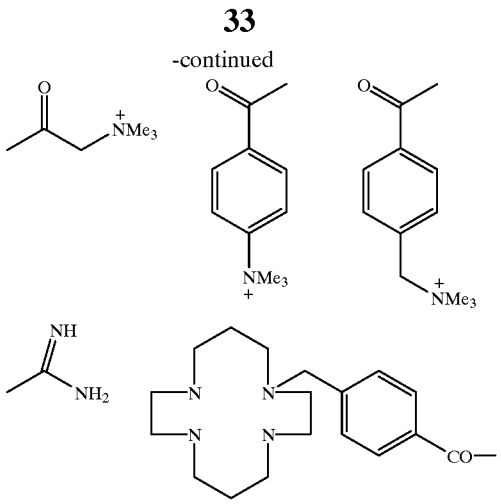

in which n is zero or a positive integer.

10. A composition according to claim 1 which is an alkylsulfonic acid terminated dendrimer.

11. A composition according to claim 1 which is a sulfoacetamide terminated dendrimer.

12. A composition according to claim 1 which is a sulfosuccinamic acid terminated dendrimer.

13. A composition according to claim 1 which is a N-(2-sulfoethyl) succinamide terminated dendrimer.

14. A composition according to claim 1 wherein the moiety bonded to the terminal groups of the dendrimer is an aryl or heteroarylthiourea substituted with at least one sulfonic acid group.

15. A composition according to claim 14 wherein the dendrimer is a 4-sulfophenylthiourea terminated group.

16. A composition according to claim 14 wherein the dendrimer is a 3,6-disulfonapthylthiurea terminated dendrimer.

17. A composition according to claim 14 wherein the dendrimer is a 4-sulfonapthylthiourea terminated dendrimer.

18. A composition according to claim 14 wherein the dendrimer is a 3,5-di-sulfophenylthiourea terminated dendrimer.

19. A composition according to claim 14 wherein the dendrimer is a 3,6,8-tri-sulfonapthylthiourea terminated dendrimer.

20. A composition according to claim 1 wherein the moiety bonded to the terminal groups of the dendrimer is an aryl or heteroaryl amide substituted with at least one group selected from the group consisting of a sulfonic acid, a sulfoalkyl, a sulfoalkoxy, a sulfoalkylamino and a sulfoalkylthio group.

21. A composition according to claim 20 wherein the dendrimer is a 4-(sulfomethyl) benzamide terminated dendrimer.

22. A composition according to claim 20 wherein the dendrimer is a 4-sulfobenzamide terminated dendrimer.

23. A composition according to claim 1 wherein the moiety bonded to the terminal groups of the dendrimer is an aryl or heteroaryl alkanamide substituted with at least one sulfonic acid group.

24. A composition according to claim 23 wherein the dendrimer is a N-(4-sulfophenyl) propanamide terminated dendrimer.

25. A composition according to claim 1 wherein the moiety bonded to the terminal groups of the dendrimer is an aryl or heteroaryl urea substituted with at least one sulfonic acid group.

26. A composition according to claim 25 wherein the dendrimer is a 4-sulfophenylurea terminated dendrimer.

27. A composition according to claim 1 wherein the moiety bonded to the terminal groups of the dendrimer is an N,N,N-trimethyl derivative of an amino acid.

28. A composition according to claim 27 wherein the dendrimer is a N,N,N-tri-methylglycinamide terminated dendrimer.

29. A composition according to claim 1 wherein the moiety bonded to the terminal groups of the dendrimer is an aryl or heteroaryl amide substituted with a group selected from the group consisting of trialkylamino, trialkylaminoalkyl, trialkylaminoalkyloxy, trialkylamioalkylamino and trialkylaminoalkylthio group.

30. A composition according to claim 29 wherein the dendrimer is a 4-trimethylammonium benzamide terminated dendrimer.

31. A composition according to claim 29 wherein the dendrimer is a 4-(trimethylammonium methyl) benzamide terminated dendrimer.

32. A composition according to claim 1 wherein the dendrimer is a N-(2-acetoxyethyl-N,N-(dimethylammonium) methylcarboxyamide terminated dendrimer.

33. A composition according to claim 1 wherein the dendrimer is a guanidino terminated dendrimer.

34. A composition according to claim 1 wherein the dendrimer is a macrocyclic polyamino group comprising a macrocyclic ring connected through an alkyl or aryl spacer moiety to the terminal group of the dendrimer.

35. A composition according to claim 34 wherein the dendrimer is a 4-([1,4,8,11-tetra-azacyclotetradecane] methyl)benzamide terminated dendrimer.

36. A composition according to claim 1 wherein the dendrimer is a 4-carboxy-3-hydroxbenzylamine terminated dendrimer.

37. A pharmaceutical or veterinary composition for prophylactic or therapeutic antiviral treatment of a human or non-human animal, which comprises a composition of claim 1, in association with at least one pharmaceutically or veterinarily acceptable carrier or diluent.

38. A method for prophylactic or therapeutic antiviral treatment of a human or non-human animal, which comprises administering to said human or animal or prophylactic- or therapeutic-antiviral-effective amount of a composition of claim 1.

39. A method according to claim 38, wherein said antiviral treatment is treatment of infection by a virus selected from the group consisting of HIV1, HIV2, Hepatitis B virus, Hepatitis C virus, Bovine Viral Diarrhoea Virus, Human Influenza Virus B, Rhinovirus, Human Parainfluenza Virus, Respiratory Syncytial Virus (RSV), Varicella Zoster Virus (VSV), Human Cytomegalovirus (CMV), Epstein Bar Virus (EBV), Human Papilloma Virus (HPV), Adenovirus, Herpes Simplex Virus type 1, Herpes Simplex Virus type 2, Measles Virus, and Vesicular Stomatitis Virus (VSV).

40. A composition according to claim 1, wherein the antiviral activity is against a virus selected from the group consisting of HIV1, HIV2, Hepatitis B virus, Hepatitis C virus, Bovine Viral Diarrhoea Virus, Human Influenza Virus B, Rhinovirus, Human Parainfluenza Virus, Respiratory Syncytial Virus (RSV), Varicella Zoster Virus (VSV), Human Cytomegalovirus (CMV), Epstein Barr Virus (EBV), Human Papilloma Virus (HPV), Adenovirus, Herpes Simplex Virus type 1, Herpes Simplex Virus type 2, Measles Virus, and Vesicular Stomatitis Virus (VSV).

* * * * *